(12) United States Patent
Wild et al.

(10) Patent No.: US 8,853,486 B2
(45) Date of Patent: Oct. 7, 2014

(54) FILM FOR COVERING A WOUND

(75) Inventors: Thomas Wild, Vienna (AT); Georg Wagner, Vienna (AT); Christian Rohrer, Linz (AT); Erik Steinlechner, Baden (AT)

(73) Assignee: Lohmann & Rauscher GmbH, Schonau an der Triesting (AT)

( * ) Notice: Subject to any disclaimer, the term of this patent is extended or adjusted under 35 U.S.C. 154(b) by 289 days.

(21) Appl. No.: 13/318,121

(22) PCT Filed: Apr. 27, 2010

(86) PCT No.: PCT/EP2010/002576
§ 371 (c)(1),
(2), (4) Date: Oct. 28, 2011

(87) PCT Pub. No.: WO2010/124844
PCT Pub. Date: Nov. 4, 2010

(65) Prior Publication Data
US 2012/0046587 A1    Feb. 23, 2012

(30) Foreign Application Priority Data
Apr. 30, 2009   (DE) .................. 10 2009 019 646

(51) Int. Cl.
*A61F 13/512* (2006.01)
*A61M 1/00* (2006.01)
*A61F 13/02* (2006.01)
*A61F 13/00* (2006.01)

(52) U.S. Cl.
CPC ....... *A61F 13/00* (2013.01); *A61F 2013/00536* (2013.01); *A61M 1/0088* (2013.01); *A61F 13/02* (2013.01); *A61F 13/00995* (2013.01); *A61F 2013/0054* (2013.01)
USPC ........... 602/43; 602/47; 604/308; 604/385.23

(58) Field of Classification Search
CPC .................................................. A61F 13/512
USPC ............. 602/42–43, 46–48, 52–54; 604/286, 604/289–290, 304–308, 313, 385.23
See application file for complete search history.

(56) References Cited

U.S. PATENT DOCUMENTS

| 6,180,132 | B1 * | 1/2001 | Huang et al. .................. 424/445 |
| 7,270,721 | B2 * | 9/2007 | Hilfenhaus et al. ............. 156/60 |

(Continued)

FOREIGN PATENT DOCUMENTS

| DE | 202006015547 U1 | 1/2007 |
| DE | 102006017194 A1 | 10/2007 |

(Continued)

OTHER PUBLICATIONS

International Preliminary Report on Patentability in International Patent Application No. PCT/EP2010/002576 dated Nov. 15, 2011.

(Continued)

*Primary Examiner* — Patricia Bianco
*Assistant Examiner* — Camtu Nguyen
(74) *Attorney, Agent, or Firm* — Schwabe Williamson & Wyatt PC

(57) ABSTRACT

Embodiments of the invention relate to a wound covering having a first strip-like element forming a first periphery and a second strip-like element that faces away from the first periphery, runs approximately parallel thereto, forming a second periphery, and is joined to the first strip-like element, there being formed between the first inner periphery of the strip-like element, facing away from the first periphery, and a second inner periphery of the second strip-like element, facing away from the second periphery, a drainage chamber, the depth of which in a depth direction extending at right angles to the periphery ensures a capillary action on bodily fluids received in the drainage chamber, in particular exudates.

18 Claims, 2 Drawing Sheets

(56) References Cited

U.S. PATENT DOCUMENTS

| | | |
|---|---|---|
| 7,381,859 B2 | 6/2008 | Hunt |
| 2004/0030304 A1 | 2/2004 | Hunt |
| 2010/0106106 A1* | 4/2010 | Heaton et al. ............ 604/290 |

FOREIGN PATENT DOCUMENTS

| | | |
|---|---|---|
| DE | 102008034362 A1 | 2/2009 |
| DE | 102007049428 A1 | 4/2009 |
| EP | 0261167 B1 | 1/1992 |
| WO | 2007/118652 A1 | 10/2007 |

OTHER PUBLICATIONS

International Search Report re PCT/EP2010/002576 dated Sep. 9, 2010.

* cited by examiner

FILM FOR COVERING A WOUND

CROSS REFERENCE TO RELATED APPLICATIONS

The present application is a 35 U.S.C. §371 national phase entry application of International Patent Application No. PCT/EP2010/002576, filed Apr. 27, 2010, which claims priority to German Patent Application No. DE102009019646.3, filed Apr. 30, 2009, the disclosures of which are hereby incorporated by reference in their entirety for all purposes except for those sections, if any, that are inconsistent with this specification.

TECHNICAL FIELD

Various embodiments of the invention relate to a wound covering having a first strip-like element forming a first periphery and a second strip-like element that faces away from the first periphery, runs approximately parallel thereto, forming a second periphery, and is joined to the first strip-like element, as well as to a wound care kit comprising such wound covering and a method for manufacturing wound coverings according to the invention.

BACKGROUND

Wound coverings are required for various disease patterns or traumata, particularly in the area of the open abdomen, where a temporary covering of the open wound or the open abdomen is required. This can be necessary, for example, where several procedures are required daily to facilitate quick access to the internal organs, on the one hand, and to avoid a disadvantageous influence of exudate formation in the area of the wound, on the other hand. A significant decrease of mortality for some indications can be achieved by means of a temporary covering.

Two main requirements are basically made from the medical view on suitable wound coverings for the mentioned application purposes. On the one hand, a good exudate management in the area of the wound, particularly for applications in the open abdomen, must be achieved, i.e. removal by suction in the entire area of the wound or the entire abdomen. In addition to that, a decrease of friction should be achieved between organs and peritoneum and the wound covering, whereas the wound is simultaneously screened well from the environment. In addition to that, it must be secured that no decontamination can reach the open wound or the open abdominal area through the wound covering.

EP 0 261 167 B1 describes a wound covering permeable to fluid and provided for direct contact with the wound base, having a hydrophobic layer to prevent adherence of the wound covering to the area of the wound and a decontamination of the wound caused thereby, as the case may be. The wound covering described in this document, however, does not achieve a satisfactory exudate management in the area of the wound.

To improve exudate management in the area of the wound, U.S. Pat. No. 7,381,859 B2 suggests a wound covering, where a foam-like layer is incorporated between two foil-like, strip-like elements permeable to water, which can be designed as plastic films, in which exudates can be absorbed. Is has proven to be problematic for the wound covering known from this document, however, that no satisfactory removal by suction of exudates can be facilitated at the edge of the wound so that complications occur during wound care in such areas.

WO 2007/118652 A1 describes a subtle thermoplastic section of material, onto which absorbent secondary dressings can be applied without adhesion and which is provided with a rough handle and a plurality of three dimensional perforations to form a first smooth surface and a second surface. When applying these known wound coverings the downstream absorption bodies are interchangeable to provide satisfactory wound care for a longer period of time. It has proven to be problematic when applying the wound covering systems described in this document, however, that satisfactory exudate management cannot be achieved over the entire area of the wound, particularly in the abdominal area.

BRIEF DESCRIPTION OF DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

DETAILED DESCRIPTION OF EMBODIMENTS

Figure 1:
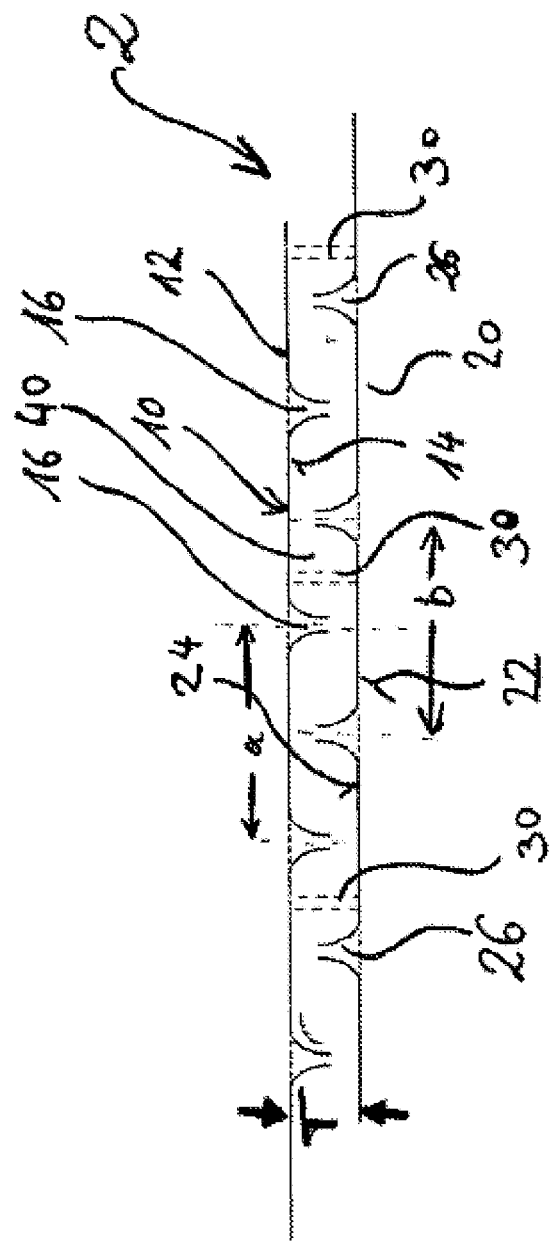
FIG. 1 is a schematic illustration of a wound covering according to various embodiments of the invention.

In view of the aforementioned described problems in the prior art, it is the object of various embodiments of the invention to provide a wound covering, whereby a good exudate management over the entire area of the wound is possible without decontamination of the wound itself.

This object is achieved according to embodiments of the invention by means of a further design of the known wound coverings, essentially characterized in that at least one drainage chamber is formed between a first inner periphery of the first strip-like element facing away from the first periphery and a second inner periphery of the second strip-like element facing away from the second periphery, the depth of which provides a capillary action in a depth direction extending at right angles to the peripheries onto the bodily liquids received into the drainage chamber, in particular exudates.

The wound covering according to embodiments of the invention achieves a capillary action between the individual strip-like elements by forming the drainage chamber, by means of which drainage of bodily fluids, in particular exudates, from the drainage chamber is prevented, on the one hand, and distribution of the bodily fluids over the entire drainage area is possible, on the other hand, without additional measures, such as providing additional absorption bodies, being absolutely necessary. In this manner, a good exudate management is facilitated over the entire area of the wound, also because no edge areas without capillary function negatively influencing the exudate management are necessary. The wound covering according to the invention can be cut to any size or any structure of wounds problem-free, particularly in the area of the abdomen, and facilitates the desired drainage function over the entire area of the wound covering. In doing so, the wound covering can be designed with a smooth surface, as well, which prevents adhesion of tissue and cell wound base or to the surrounding organs. Access of bodily fluids into the drainage chamber can be ensured when applying the wound coverings according to the invention by the fact that the strip-like elements themselves are made from a material permeable to fluid.

Within the scope of embodiments of the invention it has proven to be particularly favorable, however, if at least one of the strip-like elements comprises an opening facilitating the passage of bodily liquids into the drainage chamber. In doing so, the stability of the entire structure of wound coverings according to the invention can be improved if at least one opening is formed by a channel, which extends from one strip-like element in the direction of the opposite inner periphery of the other strip-like element and opens into the drainage chamber, the channel wall of which is preferably designed integral with the strip-like element, particularly by means of perforation of the strip-like element.

For the embodiment of the invention described last, the exudate management can be improved particularly effectively if the cross sectional area of the channel decreases in a plane at right angles to the depth direction beginning from the strip-like element in the direction of the opposite inner periphery, particularly to achieve a capillary action facilitating the access of bodily fluids into the drainage chamber. In this manner, removal of exudate from the area of the wound is supported, on the one hand, and reflux from the drainage chamber into the area of the wound is prevented, on the other hand.

The desired removal of exudate for wound coverings according to the invention can be achieved by ensuring a satisfactory overall stability of the wound covering, if at least one strip-like element has a plurality of openings, arranged preferable grid-like, particularly in a rectangular grid, with the distance between the adjacent openings or grid points being 15 mm or less, preferably 5 mm or less, particularly 3 mm or less.

With respect to the desired overall stability of the wound coverings according to embodiments of the invention it has furthermore proven to be particularly suitable if the outlets of the openings arranged in one of the strip-like elements are arranged in a projection along the depth direction between the outlets of the openings arranged at the other strip-like element.

Such arrangement of the openings in wound coverings according to embodiments of the invention can be applied particularly advantageously for openings formed by channels if the wound covering is used in connection with a negative pressure source to suction the exudate from the area of the wound, particularly the area of the abdomen, to thus prevent a collapse of the overall structure upon applying negative pressure. In this connection it has proven to be particularly favorable if at least one channel, which forms an opening in a strip-like element, extends in depth direction over 50% or more of the entire depth of the drainage chamber.

To ensure the desired permeability of the strip-like elements it has proven to be suitable if the outlet area of the individual openings facing the drainage chamber is 0.1 $mm^2$ or more, particularly 0.5 $mm^2$ or more, particularly preferred 1 $mm^2$ or more in a plane extending at right angles to the depth direction. The desired capillary action can be achieved by preventing a reflux of liquid from the drainage chamber into the area of the wound if the outlet area of the openings is 5 $mm^2$ or less, particularly 4 $mm^2$ or less, particularly preferred 3 $mm^2$ or less.

As already explained above, the channels forming the openings in the strip-like elements can be formed by means of perforation in the strip-like elements. In this context, it has proven to be favorable to achieve a smooth surface by means of which an adhesion of tissue or cells to the wound base or to the surrounding organs can be suppressed effectively, if the channel wall is designed arc-shaped, at least sectionally, in a sectional plane parallel to the depth direction and extends continuously into the periphery of the strip-liked element. The connection of the strip-like elements can be implemented with simultaneous securing of the drainage chamber effecting the drainage effect by means of punctuated attachment areas preferably designed in a grid layout. Attachment can be implemented by means of welding, adherence, or other types of solid connections. In doing so, the connection should not obstruct but support the removal of exudates. In this connection, it has proven to be favorable if the individual attachment areas comprise an area of 5 $mm^2$ or less, particularly 3 $mm^2$ or less, particularly preferred 2 $mm^2$ or less in a sectional plane extending at right angles to the depth direction, with the distance between individual attachment areas or individual grid points of the attachment areas designed in a grid layout being 2 mm or more, particularly 3 mm or more, particularly preferred 5 mm or more.

Regardless of the fact if the attachment is being implemented by means of welding, adherence, or other types of connection a material bridge can be formed in the attachment areas, connecting the inner peripheries of the strip-like elements to each other. To achieve the desired capillary action in the drainage chamber the distance between the inner peripheries of the strip-like elements is 5 mm or less, preferably 4 mm or less, particularly preferred 2 mm or less for wound coverings according to the invention. The distribution of the exudates over the entire area of the wound can be ensured by utilizing the capillary action in the drainage chamber if the distance between the inner peripheries of the strip-like elements is 0.05 mm or more, particularly 0.1 mm or more, particularly preferred 0.3 mm or more.

At least one strip-like element for wound coverings according to embodiments of the invention can comprise a preferably perforated plastic foil, and particularly be designed in the form of a perforated plastic foil as a whole.

The wound covering according to embodiments of the invention can be utilized with particular advantage in combination with negative pressure for wound care. In doing so, the wound covering according to embodiments of the invention is applied as a wound dressing or as a direct interface between wound base (tissue, cells) and the wound filer or the area of exudate removal. The wound covering according to embodiments of the invention is suitable with particular advantage for use with wounds in the open abdomen. The wound covering according to embodiments of the invention is set over the organs (intestines) in the entire abdominal area, with the wound covering offering a drainage function and a very good smooth surface to prevent an adherence or friction of tissue and foil. The wound covering according to embodiments of the invention can be anatomically preformed but also be designed to be cut to size for specific conditions. For applications in combination with negative pressure therapy, a filling media such as gauze or foam is filled-in onto the wound covering according to embodiments of the invention until the area is covered up to the skin periphery. If necessary, a tubular wound drainage can be inserted into this wound filler. The tube used to remove exudates or for wound drainage is guided out of the abdominal area and connected to a negative pressure source, which can be secured by means of a pump or a central utility in a hospital. Finally, the wound is sealed occlusively with an adhesive foil. Exudate can be removed from the entire abdominal area with the negative pressure source by means of the wound covering according to embodiments of the invention, achieving a good exudate management. The foil for the occlusive covering of the wound is responsible for the shielding of the internal organs from the environment and regulates humidity and temperature. Furthermore, it is a barrier comparable to the skin against bacteria, viruses and germs.

As can be derived from the above illustration, a wound care kit according to embodiments of the invention has a wound covering according to the invention, an absorption body arranged thereon, such as a foam body or a gauze body, an occlusive foil and a tubular removal element, if required, which can be connected to a negative pressure source.

A method to manufacture wound coverings according to embodiments of the invention is essentially characterized in that a strip-like material is perforated by e.g. using a punch wheel to form funnel-shaped openings, two perforated sections of the strip-like material are set on top of another with funnel openings facing each other and are subsequently joined to one another by means of a spot-welding method. For such method, the desired distance between the inner peripheries can be ensured by the depth of the funnel-shaped openings. In doing so, the perforation process, however, can only be implemented with limited exactness, so that—even if some funnel openings are in contact with the opposite inner periphery of the opposite strip-like element—other funnel openings still open freely into the drainage chamber.

With respect to the prevention of the adherence propensity of wound coverings according to embodiments of the invention, at least one strip of material can comprise a hydrophilic or hydrophobic equipment. Furthermore, application of swellable material has been given thought, as well.

Between the individual strips of material an absorption media, such as foam, mull, or a very open-pored material, can be provided within the drainage chamber, particularly layered. Application of super absorbents or other storage material between the strips of material is provided for within the scope of embodiments of the invention.

Below, various embodiments of the invention are illustrated by reference to drawings to which express reference is made regarding all particulars, which are essential to embodiments of the invention and have not been emphasized more closely in the description.

The wound covering illustrated in FIG. 1 includes a first strip-like element 10 comprising an outer periphery 12 as well as a second strip-like element 20 comprising an outer periphery 22. A drainage chamber 40 is formed between an inner periphery 14 of the first strip-like element 10 facing the second strip-like element 20 and an inner periphery 24 of the second strip-like element 20 facing the first strip-like element 10. The depth of the drainage chamber 40 running in a direction at right angles to the main surfaces of the strip-like elements 10 and 20, amounts to between 0.1 and 4 mm for the exemplary embodiment of the invention illustrated in the drawing.

The first strip-like element 10 comprises a plurality of grid-like channel-shaped perforations 16. The channel walls of channels 16 are designed arc-shaped in a sectional plane parallel to the depth direction and smoothly proceed into the outer periphery 12 of the first strip-like element 10. The second strip-like element 20 similarly comprises a number of perforations 26, which are arranged grid-like and channel-shaped, as well. Channels 16 and 26 extend over more than half of the entire depth of drainage chamber 40, respectively. In doing so, channels 16 and 26 are arranged such that a projection of the channel openings of channels 16 is positioned in the direction of depth between the channel openings of channels 26.

In the outlet area, the conically designed channels 16 or 26, illustrated by means of the drawing of the embodiments of the invention, comprise a diameter of from 0.2 to 1 mm. The strip-like elements 10 and 20 are joined to one other by means of material bridges 30, which are arranged grid-like. Material bridges 30 adjust the distance between the peripheries 14 and 24. The connection areas 30 can be realized by means of welding, adherence or other types of solid connections. The strip-like elements 10 and 20 can be realized in the form of plastic foils. In this connection, both synthetic plastics, such as PE, PP, PET, polyurethane (PUR), Teflon (PTFE) and foils based on biological plastics or renewable plastics such as polyhydroxybutyrate (PHB), polyacetate (PLA), polylactic acid, raw materials based on cellulose (CMC), etc. can be used. The structure of the perforated strips of material can be created by means of a non-woven manufacturing process. In doing so, both synthetic and natural (e.g. silk, cotton), fibers as well as inorganic fibers (glass ceramics . . . ) or metal (silver fibers) can be used for manufacturing the non-woven or the tissue. Within the scope of the invention, thought has also been given to the fact that strips of material 10, 20 or the drainage chamber 40 can be equipped with an antibacterial or bacteriostatic layer. The antibacterial or bacteriostatic effect can be realized by means of e.g. PHMB, silver, chlorhexidine, etc.

Figure 2:
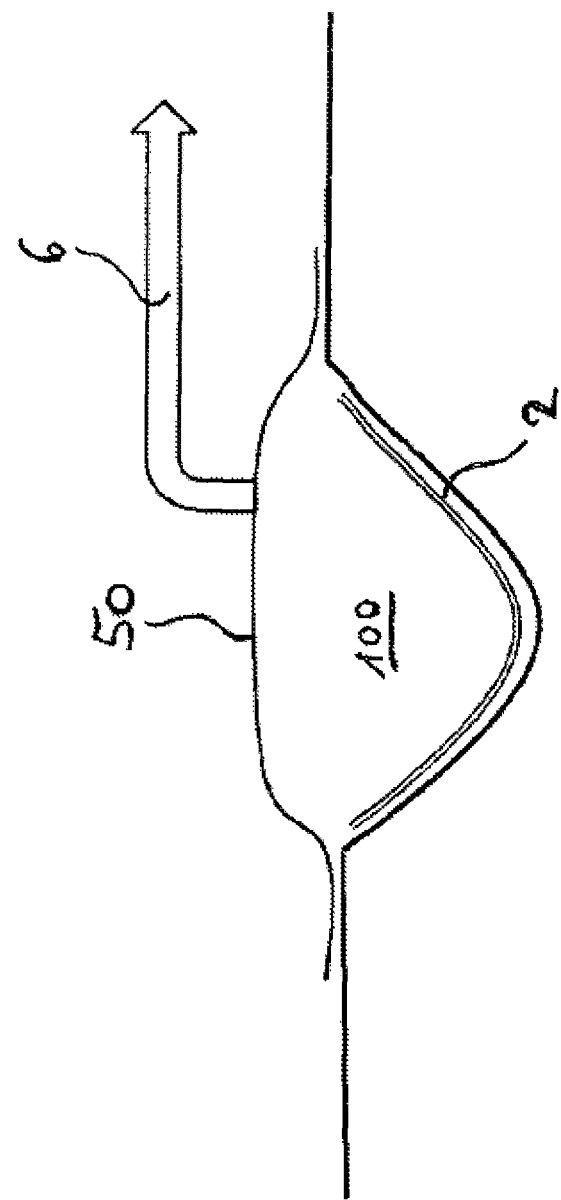
FIG. 2 is an exemplary embodiment of a wound care kit according to various embodiments of the invention.

Pursuant to the exemplary embodiment illustrated in FIG. 2, the wound covering 2 is set onto the wound, the wound is subsequently filled-in with a filling material such as foam, gauze, or the like and covered with an occlusive foil 50. The occlusive foil 50 is interspersed by an exudate line 6, which can be connected to a negative pressure source to suction the exudate from the area of the wound.

The following advantages result from the application of the wound coverings according to the invention, as illustrated above:

The pores support removal of exudate and prevent reflux of exudate into the area of the wound (capillary action) due to their inwardly elevated structure.

The open drainage chambers provide capillary action to the drainage layer 40 and thus do not allow any reflux from the wound covering.

The smooth surface obtained due to the smooth transition between the channels 16 or 26 and the outer peripheries 12 or 24 of the strip-like elements prevents an adherence of tissue or cells to the wound base or the surrounding organs.

The combination of pore size and smoothness of the foil prevents ingrowth or adherence of tissue.

The drainage chamber 40 always offers an open chamber for removal of exudate.

The wound covering can be cut to any size or structure in the wound or abdominal area without impairing the drainage function.

Finally, it is pointed out that the distance between the center axis of channels 16 or 26, as indicated in FIG. 1 at a and b, is minimally 0.1 mm and maximally 4 mm based on the exemplary embodiments of the invention illustrated by the drawing.

Embodiments of the invention are not limited to the exemplary embodiment illustrated by the drawing. In fact, wound coverings with differently embodied openings and/or multi-layered structure to form two, three, or more drainage chambers arranged on top of another are conceivable. In this case, the peripheries facing away from the inner periphery of the strip-like elements do not form an outer periphery, at least for the inlying strips of material.

The invention claimed is:

1. A wound covering with a first strip element forming a first periphery and a second strip element that faces away from the first periphery, runs approximately parallel thereto, forming a second periphery, and is joined to the first strip element, characterized in that there is formed at least one drainage chamber between a first inner periphery of the first strip element, that faces away from the first periphery and a second inner periphery of the second strip element that faces away from the second periphery, the drainage chamber having a depth (T) in a direction extending at a right angle to the first or second periphery ensures a capillary action on bodily fluids received in the drainage chamber, in particular exudates,
   wherein at least one of the first and second strip elements comprises at least one opening facilitating passage of bodily fluids into the drainage chamber,
   wherein the opening is formed by a channel, which opens into the drainage chamber and extends from the at least one of the first and second strip elements in a direction of an inner periphery of another of the first and second strip elements the channel having a channel wall which is integral with the at least one of the first and second strip elements, particularly by means of perforation of the at least one of the first and second strip elements, and
   wherein the channel extends in depth direction over 50% or more of the depth (T) of the drainage chamber.

2. The wound covering according to claim 1, characterized in that at least one of the first and second strip elements comprises a plurality of openings with the distance between the adjacent openings being 15 mm or less, particular 5 mm or less, particularly 3 mm or less.

3. The wound covering according to claim 2, wherein the openings are arranged in a grid-like fashion.

4. A method to manufacture a wound covering according to claim 1, whereby a strip material is perforated, for example by using a punch wheel to form openings, two perforated sections of the strip material are set on top of another with openings facing another, and are subsequently joined to one another.

5. The wound covering according to claim 2, characterized in that outlets of the openings arranged in the at least one of the first and second strip elements are arranged in a projection along the depth direction between the outlets of the openings arranged in the other strip element.

6. The wound covering according to claim 1, characterized in that the cross sectional area of channel decreases in a plane extending at a right angle to the depth direction beginning with the at least one of the first and second strip elements in the direction of the opposite other periphery, to achieve a capillary action regarding access of bodily fluids into the drainage chamber.

7. The method according to claim 4, wherein the openings are funnel-shaped.

8. The wound covering according to claim 1, characterized in that an outlet area of the individual openings facing the drainage chamber is 0.1 mm$^2$ or more, particularly 0.5 mm$^2$ or more, preferred 1 mm$^2$ or more in a plane running at right angles to the depth direction.

9. The wound covering according to claim 1, characterized in that an outlet area facing the drainage chamber is 50 mm$^2$ or more, 5 mm$^2$ or more, 4 mm$^2$ or more, or 3 mm$^2$ or more in a plane running at a right angle to the depth direction.

10. The wound covering according to claim 1, characterized in that the channel wall is designed arc-shaped, at least sectionally, extending in a sectional plane parallel to the depth direction and extends continuously into the first or second periphery of the first or second strip element.

11. The wound covering according to claim 1, characterized in that the first and second strip elements are joined to one another by means of punctuated attachment areas that are implemented in a grid layout.

12. The wound covering according to claim 1, characterized in that the individual attachment areas comprise an area of 5 mm$^2$ or less, 3 mm$^2$ or less, 2 mm or less in a cross sectional plane extending to the depth direction.

13. The wound covering according to claim 11 or 12, characterized in that a material bridge is formed in the attachment areas, which connects the inner peripheries of strips of material.

14. The wound covering according to claim 1, characterized in that the distance between the inner peripheries is 5 mm or less, 4 mm or less, or 2 mm or less.

15. The wound covering according to claim 1, characterized in that the distance between the inner peripheries is 0.05 mm or less, 0.1 mm or less, or 0.3 mm or less.

16. The wound covering according claim 1, characterized in that at least one of the first and second strip elements comprises a perforated plastic foil.

17. The wound covering according to claim 1, characterized in that at least one of the first and second strip elements comprises an antibacterial or bacteriostatic material, selected from a group that includes PHMB, silver, or chlorhexidine, particularly in the form of a surface layer.

18. The wound covering according to claim 1, characterized in that at least one of the first and second strip elements comprises a material, including a hydrophilic or hydrophobic equipment or an application of swellable material.

* * * * *